United States Patent [19]

Tsutsumi et al.

[11] Patent Number: 4,510,070
[45] Date of Patent: Apr. 9, 1985

[54] EMULSIFYING COMPOSITION

[75] Inventors: Hisao Tsutsumi, Miyashiro; Tomoko Inoue, Yokohama, both of Japan

[73] Assignee: Kao Corporation, Tokyo, Japan

[21] Appl. No.: 443,640

[22] Filed: Nov. 22, 1982

[30] Foreign Application Priority Data

Mar. 29, 1982 [JP] Japan .................... 57-49180

[51] Int. Cl.³ .............................................. C11D 3/36
[52] U.S. Cl. ................... 252/351; 252/174.16; 252/DIG. 17
[58] Field of Search ........... 252/351, 174.16, DIG. 17

[56] References Cited

U.S. PATENT DOCUMENTS 4,139,485  2/1979  Imokawa et al. .............. 252/174.16

OTHER PUBLICATIONS

Hackh's Chemical Dictionary—Fourth Edition—Grant, J.—Editor, McGraw-Hill Book Company, New York, San Francisco, Toronto, London, Sydney.

Primary Examiner—John Kight
Assistant Examiner—Marvin L. Moore
Attorney, Agent, or Firm—Oblon, Fisher, Spivak, McClelland & Maier

[57] ABSTRACT

Disclosed herein is an emulsifier or emulsifying composition which comprises one or more of the hydroxyalkyl or hydroxyalkenyl phosphates represented by the general formula (I) and/or (II):

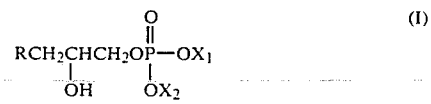

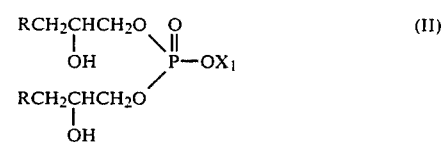

in which R represents an alkyl or alkenyl group of 5–21 carbon atoms, $X_1$ and $X_2$ independently represent a pair ion selected from the group consisting of hydrogen, alkali metal, ammonium, etc.

The emulsifying composition according to the invention is highly safe to skin and widely usable in the emulsification of either W/O or O/W type.

14 Claims, 3 Drawing Figures

EMULSIFYING COMPOSITION

BACKGROUND OF THE INVENTION (i) Field of the Invention

This invention relates to an emulsifying composition and more particularly, to an emulsifying composition which comprises an hydroxyalkyl or alkenyl phosphate or a salt thereof thereby ensuring good feeling to the touch and low irritation when applied to living body and particularly skin withh excellent emulsification stabilizing ability.

(ii) Description of the Prior Art

In general, compounds used as an emulsifier can broadly be classified into two groups including a hydrophilic emulsifier group which shows high solubility in water or has a great HLB value and an oleophilic emulsifier group which shows high solubility in oil or has a small HLB value. The former has conventionally been used for stabilizing mainly O/W type emulsions and the latter used for W/O type emulsions. In this connection, however, oils to be emulsified greatly vary in property depending on the type of oil and thus a required level of HLB also depends on the type of oil. Accordingly, there is little chance of using hydrophilic emulsifiers alone or oleophilic emulsifiers alone and it is general to use a mixture of both the type emulsifiers to have a suitable level of HLB value. Especially when oils to be emulsified are in the form of a mixture, such a general way of the use is the common practice.

Conventionally employed hydrophilic emulsifiers are, for example, surface active agents which include anionic surface active agents such as alkali metal salts of fatty acids, alkylsulfates and the like, and ethylene oxide-added nonionic surface active agents such as polyoxyethylene alkyl ethers, polyoxyethylene fatty acid esters, polyoxyethylene sorbitan fatty acid esters, and the like. On the other hand, oleophilic emulsifiers include, for example, nonionic surface active agents such as sorbitan-fatty acid esters, glycerine-fatty acid esters and the like.

A method of preparing emulsifier compositions having different HLB values by mixing hydrophilic emulsifiers, which are obtained by combining fatty acid-triethanolamine salts and ethylene oxide-added nonionic surface active agents, with oleophilic emulsifiers such as glycerine-fatty acid esters has been widely utilized for emulsification in order to obtain emulsion-type cosmetics such as creams, lotions and the like.

However, it has been suggested that ethylene oxide-added nonionic surface active agents contain formalin, dioxane and the like as impurities and these impurities have the alergic action on living body. Further, it is known that anionic surface active agents are generally high in skin irritativeness and are thus not favorable as an emulsifier. Accordingly, in case that the anionic surface active agents are employed, alkali metal salts of fatty acids are used by virtue of giving relatively low skin irritativeness, this case however, accompanied by another disadvantage that the resulting emulsion is rendered alkaline.

That is, emulsion-type cosmetics using these known emulsifiers are not fully satisfactory in safety.

On the other hand, it has been known that there are present in living body a group of compound having surface activity and called phospholipids, which play an important role as main components of membranes of living body. Typical examples of the phospholipids include glycerophospholipids such as phosphatidyl choline (lecithin), phosphatidyl ethanolamine (cephalin), phosphatidyl serine and the like. These phospholipids are components in vivo, and are thus surface active materials which are high in safety against living body. For instance, lecithin has been industrially utilized as an emulsifier. However, since these are of natural origin, they have various impurities and suffer deterioration in quality inherent of natural materials as time goes. Furthermore, the structure such as of a fatty acid composition cannot be arbitrarily changed, so that its HLB value cannot be changed freely. Moreover, in order to obtain emulsified cosmetics which ensure good feeling on use, it is known that relatively hydrophilic oils or polar oils are satisfactorily used as the oil phase. However, the emulsification of polar oils is comparatively difficult and sufficient emulsification stability cannot be obtained in case of using weak surface active materials such as lecithin.

SUMMARY OF THE INVENTION

Accordingly, we have made an intensive study to develop an emulsifier or emulsifying composition which exhibits good emulsification stability and high safety against living body, as a result, found that the above object can be achieved by using, as an emulsifier, a hydroxyalkyl or hydroxyalkenyl phosphate represented by the general formula (I) and/or (II)

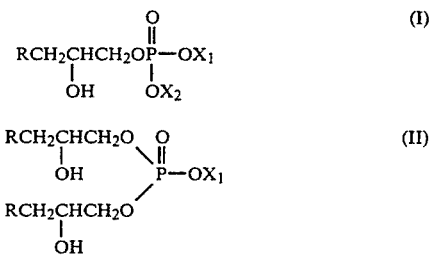

in which all the R may be the same or different and represent an alkyl or alkenyl group containing 5–21 carbon atoms, $X_1$ and $X_2$ independently represent a pair ion selected from the group consisting of hydrogen, alkali metal, ammonium, alkylammonium which has an alkyl group containing 1–5 carbon atoms, and alkanolamine which has a hydroxyalkyl group containing 2 or 3 carbon atoms.

That is, the present invention provides and emulsifier or emulsifying composition which comprises one or more of the hydroxyalkyl or hydroxyalkenyl phosphates represented by the general formula (I) and/or (II).

DETAILED DESCRIPTION OF THE INVENTION AND PREFERRED EMBODIMENTS

Figure 1:
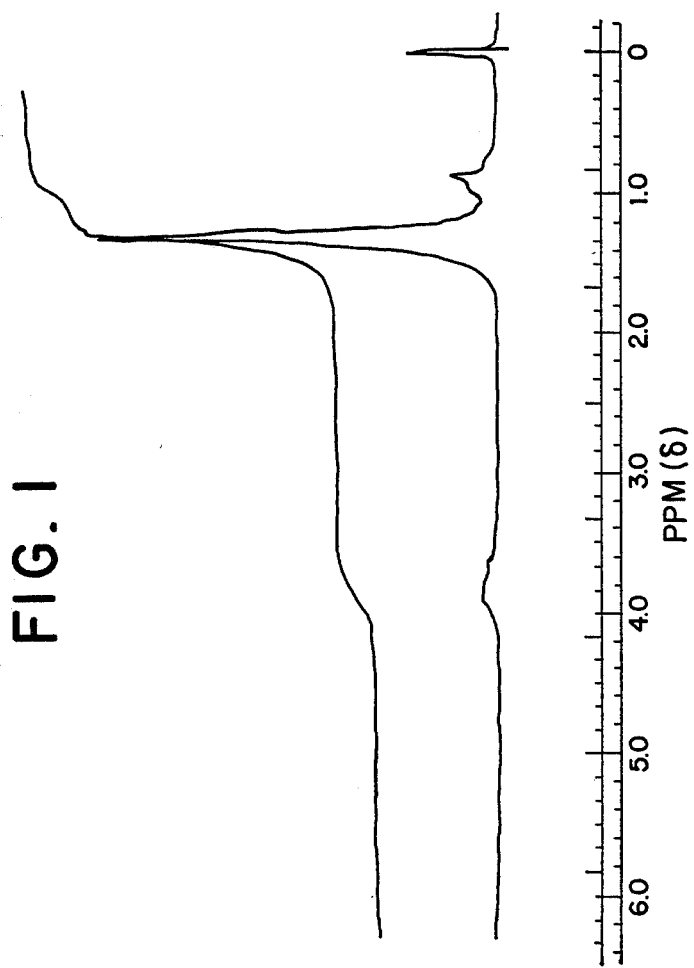
FIG. 1 is a $^1$H-NMR spectrum chart of a compound (of the formula (I) in which $R=C_9H_{19}$) of the invention.

The preparation of the hydroxyalkyl or hydroxyalkenyl phosphates used in the practice of the invention and represented by the general formula (I) and/or (II) is not critical. For instance, they can be synthesized by reacting an alkylepoxy compound or alkenylepoxy compound with phosphoric acid according to the following formula to readily prepare a phosphate and then neutralizing the phosphate with a suitable alkali agent.

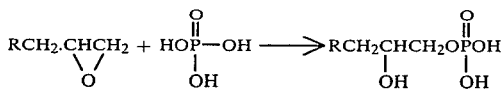

The salt may be formed by separately adding in a compounding vessel the phosphate and an alkali agent for neutralization or adjustment of the pH. In this connection, for preparing an emulsion, it is preferable to use a nascent emulsifying process in which the phosphate is added in the form of an acid and the emulsification is effected while being added an alkali agent.

Typical examples of the compound (a)-(f) of the present invention are shown along with their properties in Table I below.

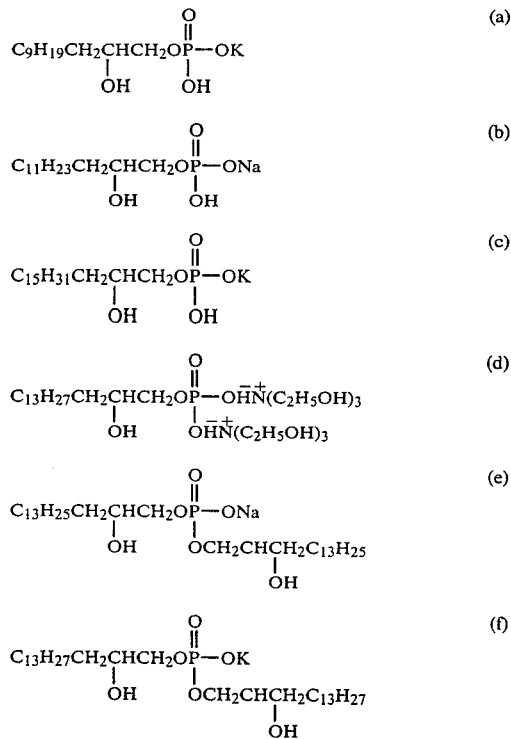

TABLE 1

| Sample | a | b | c | d | e | f |
|---|---|---|---|---|---|---|
| Appearance | White Powder | White Powder | White Powder | White Powder | White Powder | White Powder |
| Odor | Little | Little | Little | Little | Little | Little |
| Solubility in Water | | | | | | |
| (25° C.) | Good | Good | Good | Good | Good | Good |
| (70° C.) | " | " | " | " | " | " |
| pH (1%) | 5.3 | 5.4 | 6.5 | 7.5 | 5.2 | 5.8 |

The emulsifying composition according to the invention which comprises the hydroxyalkyl or hydroxyalkenyl phosphate compounds is high in safety against skin and can be held at a desired level of HLB by incorporating with oleophilic emulsifiers if necessary, with the attendant advantage that it is generally usable in the emulsification of either W/O or O/W type.

Because the emulsifying composition of the invention has such a widely applicable stabilizing effect as mentioned above, it can be utilized not only in the technical fields of medical drugs, cosmetics and food industries, but also in almost all the fields of fiber, metal, agricultural and synthetic resin industries. Above all, the composition is particularly suitable for use in the technical fields of cosmetics and medical drugs. Accordingly, hereinafter, embodiments in the field of cosmetics are described.

Since the use of compositions such as cosmetics requires a degree of safety on contact with the skin, proper selection of the pair of ions in the hydroxyalkyl or hydroxyalkenyl phosphate compound is needed. That is, when the pair ions $X_1$ and $X_2$ in the hydroxyalkyl or hydroxyalkenyl phosphate compound represented by the general formula (I) and/or (II) are both hydrogen, the composition becomes too acidic in nature. On the contrary, when both ions are an alkali metal, the alkalinity becomes excessive. Accordingly, both ions should not be hydrogen or an alkali metal. To avoid the above, the pH of the emulsifying composition is controlled to have a range of 4–9, preferably 5–7.

The preferred species for the purpose of the invention include sodium, potassium, triethanolammonium, ammonium and hydrogen. Above all, combinations of $X_1=H$ and $X_2=K$, $X_1=H$ and $X_2=Na$, $X_1=H$ and $X_2=$triethanolamine, $X_1=X_2=$triethanolamine, and $X_1=H$ and $X_2=$ammonium are preferably used.

Among the hydroxyalkyl or hydroxyalkenyl phosphate compounds represented by the general formula (I) and/or (II), hydroxyalkyl phosphate salts are preferably used. Moreover, R in the general formula (I) and/or (II) has preferably 9–15 carbon atoms.

The phosphate compounds of the general formulas (I) and (II) can be used singly or in combination at arbitrary ratios depending on the type of oil to be emulsified. Preferably, the weight ratio of the compounds of the general formula (I)/ the general formula (II) is preferably in the range of 100/0–20/80.

Oleophilic emulsifiers used as required may not be critical and those which contain no ethylene oxide groups therein are preferably used. Examples of such emulsifiers include sorbitan fatty acid esters, glycerine fatty acid esters, sucrose fatty acid esters, propylene glycol fatty acid esters and the like. These are used as mono- or di-esters of fatty acids having 10 to 20 carbon atoms and may be used singly or in combination.

The emulsion-type cosmetics using the emulsifiers of the present invention can be prepared, according to a usual manner, by compounding the emulsifiers and known cosmetic ingredients such as, for example, a cosmetic oily substrate, surface active agent, viscosity modifier, medical agents, preservative and other wetting agents.

The cosmetic oily substrates are, for example, hydrocarbons such as liquid paraffin, paraffin wax, ceresine, squalane, bees wax, spermaceti, carnauba wax, natural animal and plant oil, olive oil, tsubaki oil, jojoba oil, lanolin, and silicone oils, fatty acids, higher alcohols and ester oils obtained by reacting these oils. Examples of the surface active agents include polyoxyethylene alkyl ethers, polyoxyethylene fatty acid esters, polyoxyethylene sorbitan fatty acid esters, polyoxyethylene sorbitol fatty acid esters, polyoxyethylene hardened castor oil, alkylsulfates, polyoxyethylene alkylsulfates, alkyl phosphates, polyoxyethylene alkyl phosphates, and alkali metal salts of fatty acids and the like. These agents are added in such an amount that the effect of the invention is not impeded. Further, the viscosity modifiers include polymer compounds such as polyvinyl alcohol, carboxyvinyl polymer, carboxymethyl cellulose, polyvinylpyrrolidone, hydroxyethyl cellulose, methyl cellulose, natural gelatin, tragacanth gum, and alcohols. Medical agents are, for example bactericides, antiphlogistics and vitamins and the like. The wetting agents include propylene glycol, glycerine, 1,3-butylene glycol, sorbitol, dipropylene glygol, lactic acid, and sodium lactate, sodium pyrrolidonecarboxylate and the like. The preservatives include paraoxybenzoates, benzoic acid, sodium benzoate, sorbic acid, potassium sorbiate, and phenoxyethanol and the like.

Preferred compositions of the emulsion-type cosmetic according to one embodiment of the invention are as follows.

|  | Compounding Amount (wt %) | Preferable Compounding Amount (wt %) |
|---|---|---|
| Cosmetic oily substrate | 1–60 | 5–35 |
| Emulsifier [general formula (I) and/or (II)] | 0.1–10 | 0.5–7 |
| Viscosity modifier. etc. | 0–10 | 0–5 |
| Medical agent | 0–10 |  |
| Wetting agent | 0–30 | 0–10 |
| Preservative | 0–1 | 0.02–1.0 |
| Water | 25–95 | 40–90 |

The emulsifier may be added after preparation or may be directly added to the compounding composition of the cosmetic.

The emulsion-type cosmetics of the invention can be used in various forms including, for example, cleansing creams, cold creams, lotions, nutritive creams, night creams, vanishing creams, foundation creams, hand creams, hair creams and the like. They may be in either type of emulsion, i.e. O/W or W/O.

The emulsion-type cosmetics thus obtained according to one embodiment of the invention exhibit excellent emulsion stability and excellent skin-protecting effect and feeling to the touch.

The present invention is particularly described by way of a synthetic example and examples.

SYNTHETIC EXAMPLE 1

Into a 2 liters round bottom flask equipped with a reflux condenser, thermometer, dropping funnel and agitator were charged 296 g (3.0 moles) of 99.5 wt% orthophosphoric acid and 500 ml of n-hexane. Into the mixture solution was dropped 184 g (oxirane value 304.5, 1.0 mole) of 1,2-epoxydodecane extending for 1.5 hours under reflux of n-hexane (65°–70° C.). After completion of the dropping, the agitation was continued at 65°–70° C. for further 5 hours. After completion of the reaction, 500 ml of diethyl ether and 500 ml of 1N hydrochloric acid were added to the reaction mixture and mixed together. The resulting mixture was transferred into a separating funnel and shaked to extract unreacted phosphoric acid in the aqueous hydrochloric acid phase. The organic phase was separated and washed with 500 ml of 1/10N hydrochloric acid, followed by removing the solvent by distillation to obtain a mixture of the phosphate and a nonionic substance. Thereafter, the mixture was neutralized with an ethanol solution of potassium hydroxide to allow the phosphate component to precipitate as the potassium salt. After removal of the ethanol by distillation, the remaining white solid was reduced into pieces and washed several times with 500 ml of hot acetone to remove the nonionic substance therefrom.

Then, the solid was separated by filtration and dried under reduced pressure to obtain the potassium salt of the phosphate. The potassium salt was dissolved in 1 liter of 6N hydrochloric acid to render the system acidic and the resulting phosphate was extracted with 500 ml of diethyl ether, followed by washing the organic phase with 500 ml of 1/10N hydrochloric acid solution and distilling off the solvent under reduced pressure to obtain 256 g of purified phosphate. The acid value (mg of potassium hydroxide required for neutralizing 1 g of the same to the first equivalence point $= AV_1 = 175.2$, mg of potassium hydroxide required for the second equivalence point $= AV_2 = 350.2$.) revealed that the phosphate was a monoester. The yield was found to be 80% (based on the epoxy compound, moisture content of 12%).

The elementary analysis was effected using a sample which had been obtained by converting the purified phosphate into a corresponding dipotassium salt with use of an ethanol solution of potassium hydroxide, separating the salt by filtration and drying under reduced pressure.

Elementary Analysis $C_{12}H_{25}O_5PK_2$: Calculated: C, 40.2; H, 7.0; P, 8.6; K, 21.8. Found: C, 40.6; H, 6.8; P, 8.8; K, 21.0.

$^1$H-NMR (CDCl$_3$, Internal Standard: Tetramethylsilane (TMS))—FIG. 1.

$\delta$0.87 ppm (t, 3H, —C$\underline{H}_3$)
$\delta$1.26 ppm (broad s, 18H, —(C$\underline{H}_2$)$_9$—)

Figure 2:
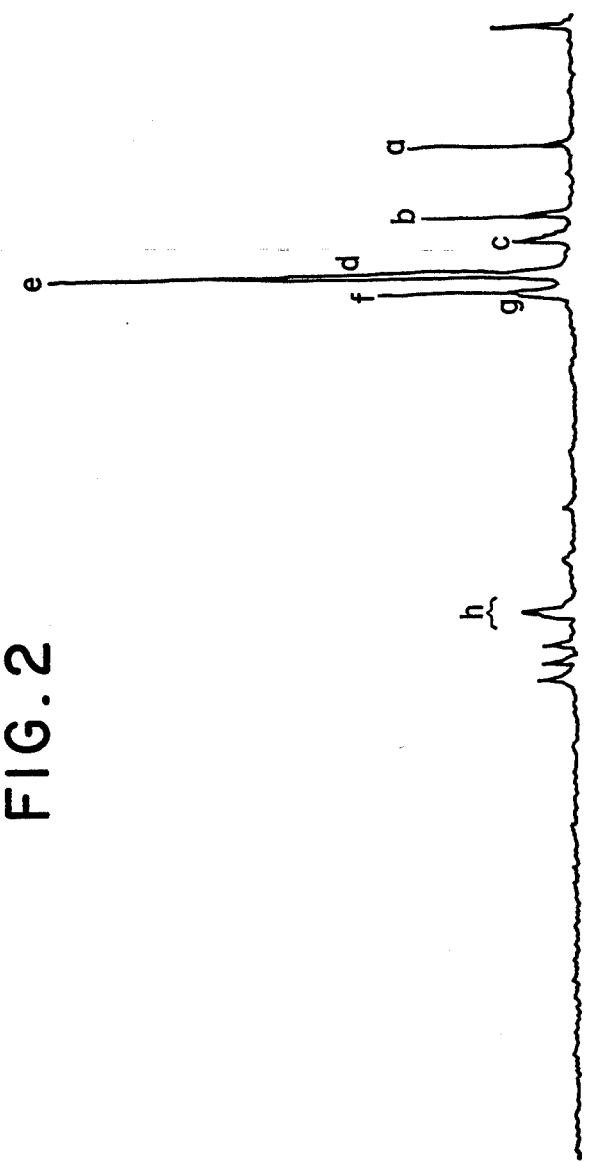
FIG. 2 is a $^{13}$C-NMR spectrum chart of the same compound as indicated above.

$\delta$3.37~4.13 ppm (broad, 3H, —C$\underline{H}$—C$\underline{H}_2$—O—)
$\qquad\qquad\qquad\qquad\qquad\qquad\quad$ |
$\qquad\qquad\qquad\qquad\qquad\qquad\;$ OH $^{13}$C-NMR (CDCl$_3$, Internal Standard TMS)—FIG. 2.

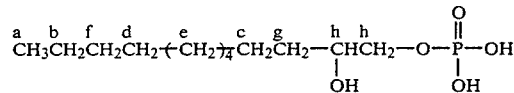

$\delta$(ppm): a 14.1, b 22.7, c 25.7, d 29.6, e 29.9, f 32.1, g 32.3, h 70.7~72.5

Figure 3:
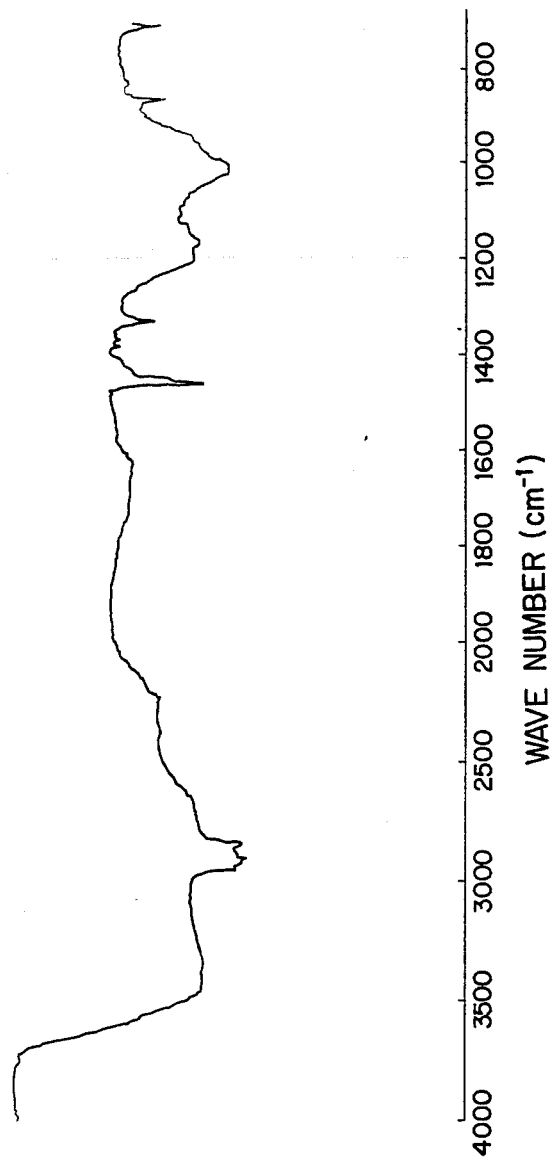
FIG. 3 is an IR spectrum chart of the compound.

IR (film)—FIG. 3.
3400, 2900, 2840, 1460, 1160, 1000 cm$^{-1}$.

EXAMPLE 1

An aqueous 10% solution of each of the compounds (a)–(f) of the present invention and comparative products was subjected to the close patch test for 24 hours in which three groups of guinea pigs, each group consisting of 6 guinea pigs, were used. After removal of the patch, the intensities of the skin reaction after 24 hours were evaluated in seven ranks including redness (±, +, ++), chemosis (±, +, ++) and negative (−). "−", "±", "+" and "++" were scored as 0, 0.5, 1.0 and 2.0, respectively, and the total score of the redness and chemosis was obtained and an average stimulative value which was an average value of 6 guinea pigs was calculated for comparing the skin stimulativeness. The results are shown in Table 2.

TABLE 2

|  | Tested Compounds | Average Stimulative Value | Other Skin Reactions |
|---|---|---|---|
| Compounds of Invention | (a) | 0.2 | Same as water |
|  | (b) | 0.2 | " |
|  | (c) | 0 | " |
|  | (d) | 0.3 | " |
|  | (e) | 0 | " |
|  | (f) | 0 | " |
| Comparative Compounds | Sodium laurylsulfate | 3.2 | Heavy falling-off waste |
|  | Sodium dodecylbenzenesulfonate | 2.0 | Moderate falling-off waste |
|  | Sodium α-dodecenesulfonate | 0.7 | Slight falling-off waste |
|  | Sodium laurylpolyoxyethylene sulfate | 0.9 | Slight gloss |

As will be apparent from the above results, the conventional anionic active agents used as the hydrophilic emulsifier exhibited a substantial degree of skin stimulativeness but the compounds of the invention exhibited little or no stimulativeness.

EXAMPLE 2

An O/W type emulsifier of the following composition was prepared to determine the pH and the stability by day of the emulsifier.

| Test oil | 25 wt % |
|---|---|
| Test emulsifier | 4 |
| Water | 71 |

The emulsification was effected by a phase inversion emulsification in which a test oil and a test emulsifier were mixed and heated to 70° C., to which water of 70° C. was gradually added while agitating. As for some of the experiments, there was used, as indicated in the results of Table 3, a nascent emulsification method in which a non-neutralized test emulsifier and a test oil were mixed together, to which was added for emulsification an aqueous solution of an alkali agent to be a paired ion. The resulting emulsions were allowed to stand over 1 month at 20° C. and 40° C. and their stability was evaluated according to the following judging standard. (Standard of Stability)

(−) No separation.
(+) Slight separation of oil component.
(++) Separation into two phases including cream phase and drainage phase.
(+++) Separation into three phase including cream phase, drainage phase and combined phase.
(++++) Disappearance of cream phase and separation into oil and water.

TABLE 3

|  |  | Test Oil | | | | | |
|---|---|---|---|---|---|---|---|
|  |  | Octyldodecanol | | | Olive Oil | | |
|  |  |  | Stability | |  | Stability | |
| Test Emulsifier | | pH | 20° C. | 40° C. | pH | 20° C. | 40° C. |
| Compounds of Invention | Mixture of compound (b) of Table 1 and monoglyceride stearate (mixing ratio 1/1)* | 6.5 | (−) | (−) | 6.5 | (−) | (−) |
|  | Mixture of compound (c) of Table 1 and compound (f) of Table 1 (mixing ratio 1/1)* | 6.6 | (−) | (−) | 6.6 | (−) | (−) |
|  | Mixture of compound (f) of Table 1 and monoglyceride stearate (mixing ratio 1/1)* | 6.5 | (−) | (−) | 6.6 | (−) | (−) |
| Comparative Compounds | Mixture of triethanolamine stearate and monoglyceride stearate* (mixing ratio 1/1) | 8.4 | (+) | (++) | 8.2 | (−) | (+) |
|  | Mixture of polyoxyethylene(20) sorbitan monostearate and monoglyceride stearate (mixing ratio 1/1) | 6.4 | (+++) | (+++) | 6.3 | (+++) | (+++) |
|  | Mixture of polyoxyethylene(20) oleyl ether and monoglyceride stearate (mixing ratio 1/1) | 6.0 | (++) | (+++) | 6.0 | (+++) | (+++) |
|  | Mixture of potassium myristate and monoglyceride stearate (mixing ratio 1/1)* | 8.4 | (+) | (+) | 8.5 | (++) | (+++) |
|  | Lecithin | 6.7 | (+++) | (+++) | 6.8 | (+++) | (+++) |

*Emulsified by a nascent emulsification.

The test results demonstrate that the phosphate salts to be compounds of the present invention have excellent ability of emulsification as a hydrophilic emulsifier, i.e. they emulsify polar and non-polar oils with equal to or higher ability than alkali metal salts of fatty acid and ethylene oxide-added nonionic active agents conventionally employed for the same purpose, and that the resulting emulsions can be made weakly acidic.

As will be apparently seen from Examples 1 and 2, the use of the phosphate compounds of the invention ensures ready preparation of emulsions of high safety.

| Example 3 Hand Cream (O/W type) | |
|---|---|
| 1. Non-neutralized product of compound (f) of Table 1 | 1.9 wt % |
| 2. Monoglyceride stearate | 2.0 |
| 3. Stearic acid | 8.0 |
| 4. Stearyl alcohol | 2.0 |
| 5. Squalane | 3.0 |
| 6. Bees wax | 0.5 |
| 7. Olive oil | 5.0 |
| 8. Butyl paraoxybenzoate | 0.1 |
| 9. Methyl paraoxybenzoate | 0.1 |
| 10. Glycerine | 4.0 |
| 11. Sodium hydroxide | 0.1 |
| 12. Perfume | suitable amount |
| 13. Purified water | balance |

1-8 were heated to 70° C. and mixed together. Separately, a mixture of 9-11 and 13 heated to 70° C. and was gradually added to the mixture of 1-8 for emulsification. Finally, 12 was added and mixed, followed by cooling and charging into a container.

| Example 4 Cold Cream (O/W type) | |
|---|---|
| 1. Non-neutralized product of compound (b) of Table 1 | 2.9 wt % |
| 2. Sorbitan sesquioleate | 2.0 |
| 3. Liquid paraffin | 25.0 |
| 4. Octyldodecanol | 10.0 |
| 5. Bees wax | 2.0 |
| 6. Vaseline | 6.0 |
| 7. Cetanol | 2.0 |
| 8. Butyl paraoxybenzoate | 0.1 |
| 9. Methyl paraoxybenzoate | 0.1 |
| 10. Glycerine | 5.0 |
| 11. Propylene glycol | 5.0 |
| 12. Perfume | suitable amount |
| 13. Purified water | balance |

1-8 were heated to 70° and mixed. Separately, a mixture of 9-11 and 13 was heated to 70° C. and gradually added to the mixture of 1-8 for emulsification. Finally, 12 was added to and mixed with the mixture, followed by cooling and charging into a container.

What is claimed is:

1. An emulsifying composition comprising one or more of hydroxyalkyl or hydroxyalkenyl phosphates represented by the general formula (I) and/or (II)

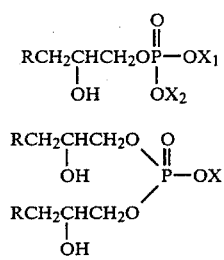

in which R may be the same or different and represent an alkyl or alkenyl group having 5-21 carbon atoms, $X_1$ and $X_2$ independently represent a pair ion selected from the group consisting of hydrogen, alkali metal, ammonium, alkylammonium whose alkyl group has 1-5 carbon atoms, and alkanolamine which has a hydroxyalkyl group having 2 or 3 carbon atoms.

2. The emulsifying composition of claim 1, wherein one of the hydroxyalkyl or hydroxyalkenyl phosphates has the formula:

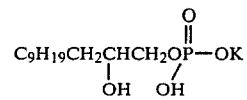

3. The emulsifying composition of claim 1, wherein one of the hydroxyalkyl or hydroxyalkenyl phosphates has the formula:

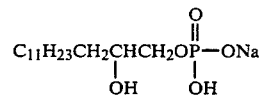

4. The emulsifying composition of claim 1, wherein one of the hydroxyalkyl or hydroxyalkenyl phosphates has the formula:

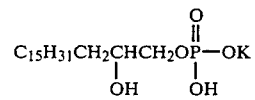

5. The emulsifying composition of claim 1, wherein one of the hydroxyalkyl or hydroxyalkenyl phosphates has the formula:

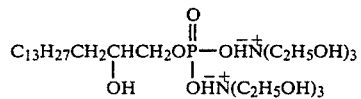

6. The emulsifying composition of claim 1, wherein one of the hydroxyalkyl or hydroxyalkenyl phosphates has the formula:

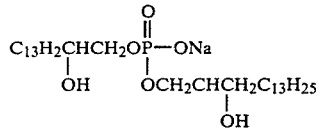

7. The emulsifying composition of claim 1, wherein one of the hydroxyalkyl or hydroxyalkenyl phosphates has the formula:

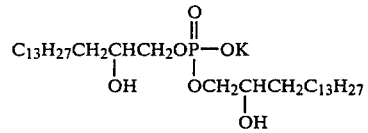

8. The emulsifying composition of claim 1, having a pH in water of between 4 and 9.

9. The emulsifying composition of claim 8, having a pH between 5 and 7.

10. The emulsifying composition of claim 8, wherein $X_1$ and $X_2$ are selected from the group consisting of sodium, potassium, triethanolammonium, ammonium and hydrogen.

11. The emulsifying composition of claim 8, wherein $X_1$ and $X_2$ are selected from the group consisting of:
$X_1=H$ and $X_2=K$;
$X_1=H$ and $X_2=Na$;
$X_1=H$ and $X_2=$ triethanolammonium;
$X_1=X_2=$ triethanolammonium; and
$X_1=H$ and $X_2=$ ammonium.

12. The emulsifying composition of claim 1, wherein R is $C_9-C_{15}$ hydrdoxyalkyl.

13. The emulsifying composition of claim 1, wherein the weight ratio of the formula (I) compounds to the formula (II) compounds is 100/0 to 20/80.

14. The emulsifying composition of claim 1, further comprising an oleophilic emulsifier selected from the group consisting of sorbitan fatty acid esters, glycerine fatty acid esters, sucrose fatty acid esters, propylene glycol fatty acid esters, in the form of mono or diesters of $C_{10}-C_{20}$ fatty acids and mixtures thereof.

* * * * *